United States Patent
Provost-tine et al.

(10) Patent No.: US 7,294,117 B2
(45) Date of Patent: Nov. 13, 2007

(54) ASPIRATION CATHETER WITH TRACKING PORTION

(75) Inventors: Michelle Provost-tine, North Andover, MA (US); Michael John Papa, Beverly, MA (US); Michael Charles Riopel, Ipswich, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 421 days.

(21) Appl. No.: 10/922,081

(22) Filed: Aug. 20, 2004

(65) Prior Publication Data

US 2006/0041246 A1    Feb. 23, 2006

(51) Int. Cl.
*A61M 29/00*   (2006.01)
(52) U.S. Cl. .............. 604/103.04; 604/164.13
(58) Field of Classification Search ............ 604/93.01, 604/95.04, 103.04, 103.09, 103.1, 510, 524, 604/526, 527, 528
See application file for complete search history.

(56) References Cited

U.S. PATENT DOCUMENTS

| | | |
|---|---|---|
| 4,917,103 A | 4/1990 | Gambale et al. |
| 4,988,356 A | 1/1991 | Crittenden et al. |
| 5,267,958 A | 12/1993 | Buchbinder et al. |
| 5,490,837 A | 2/1996 | Blaeser et al. |
| 6,152,909 A | 11/2000 | Bagaoisan et al. |
| 6,248,100 B1 | 6/2001 | de Toledo et al. |
| 6,592,548 B2 * | 7/2003 | Jayaraman ............. 604/103.04 |
| 6,730,107 B2 * | 5/2004 | Kelley et al. ................ 606/192 |
| 6,800,065 B2 | 10/2004 | Duane et al. |

FOREIGN PATENT DOCUMENTS

| WO | WO 98/39046 A1 | 9/1998 |
|---|---|---|
| WO | WO 00/69498 | 11/2000 |

OTHER PUBLICATIONS

Sater, Gabe "Catheter With a Sectional Guidewire Shaft", Nov. 14, 2003, U.S. Appl. No. 10/712,374.

* cited by examiner

*Primary Examiner*—Catherine S. Williams
(74) *Attorney, Agent, or Firm*—James F. Crittenden (57) ABSTRACT

A catheter having one or more radially expanded portions that comprise a guidewire lumen. The guidewire lumen and the main lumen of the catheter are not separate and share the same fluid space. The catheter maintains a large, circular lumen for aspiration or delivery. The catheter is made by lacing a guidewire lumen mandrel through openings made in the catheter shaft and then forcing the shaft to expand radially to create a guidewire lumen.

13 Claims, 6 Drawing Sheets

ASPIRATION CATHETER WITH TRACKING PORTION

BACKGROUND OF THE INVENTION

1. Field of the Invention

This invention relates to catheters for use within the body of a patient, and more particularly to aspiration and delivery catheters where the guidewire and aspiration or delivery lumens are not separate from each other.

2. Background of the Invention

Catheters have long been used for the treatment of diseases of the cardiovascular system, such as treatment or removal of stenosis. For example, in a percutaneous transluminal coronary angioplasty (PTCA) procedure, a catheter is used to insert a balloon into a patient's cardiovascular system, position the balloon at a desired treatment location, inflate the balloon, and remove the balloon from the patient. Another example is the placement of a prosthetic stent that is placed in the body on a permanent or semi-permanent basis to support weakened or diseased vascular walls to avoid catastrophic rupture thereof.

Often, more than one interventional catheter is used during a procedure, such as to change the size of the balloon being used or to introduce additional devices into the system to aid with the procedure, including delivery and aspiration catheters. In such situations, the catheters are generally inserted into the patient's cardiovascular system with the assistance of a guidewire. For example, a guidewire is introduced into the patient, steered through the tortuous pathways of the cardiovascular system, and positioned at a predetermined location. Various catheters having a guidewire lumen adapted to receive the guidewire may then be introduced into and removed from the patient along the guidewire, thereby decreasing the time needed to complete a procedure.

The treatment or removal of stenosis may introduce thrombi and/or emboli into the bloodstream. These particles can actually worsen a patient's condition by blocking the body lumen in the vicinity of the treatment area, or the particles can migrate to other parts of the body and create blockages in those areas. If the body lumen becomes occluded, the patient may suffer deleterious or even life-threatening effects, such as myocardial infarction or stroke.

Many techniques exist for preventing the release of thrombotic or embolic particles into the bloodstream during such a procedure. Common among these techniques is to introduce an occlusive device or a filter downstream of the treatment area to capture these embolic or thrombotic particles. The particles may then be removed from the vessel with the withdrawal of the occlusive or filtering device. In another common technique, the particles may be removed by an aspiration catheter prior to the withdrawal of these devices.

Two types of catheters commonly used in angioplasty procedures are referred to as over-the-wire (OTW) catheters and rapid exchange (RX) catheters. A third type of catheter with preferred features of both OTW and RX catheters, that is sold under the trademarks MULTI-EXCHANGE™, ZIPPER MX™, ZIPPER™, and/or MX™, is discussed below. An OTW catheter's guidewire lumen runs substantially the entire length of the catheter and is attached to, or enveloped within, the catheter shaft. Thus, the entire length of an OTW catheter is tracked over a guidewire during a PTCA procedure. A RX catheter, on the other hand, has a guidewire shaft that extends within only the distalmost portion of the catheter. Thus, during a PTCA procedure only the distalmost portion of a rapid exchange catheter is tracked over a guidewire. In both instances, the guidewire lumen and the main lumen of the catheter are separate from each other.

An aspiration catheter may be designed such that a guidewire is contained within the aspiration lumen as the catheter is advanced thereover, or the aspiration catheter may include a guidewire shaft extending along substantially the entire length of the aspiration catheter such that the guidewire is disposed therein as the catheter is advanced through a body lumen.

While over-the-wire catheters are advantageous in many ways, deploying and exchanging the aspiration catheter can be difficult. In order to maintain a guidewire in position while withdrawing an indwelling aspiration catheter, the clinician must grip the proximal end of the guidewire to prevent it from becoming dislodged during removal of the aspiration catheter. However, the aspiration catheter, which is typically on the order of 135 centimeters long, is generally longer than the exposed portion of the guidewire. Therefore, to be able to maintain the guidewire in place, the guidewire must be sufficiently long so that the clinician may be able to maintain a grip on an exposed portion of the guidewire. For aspiration catheters on the order of 135 centimeters in length, therefore, a guidewire of 300 centimeters in length is necessary. Manipulating an aspiration catheter along such a long guidewire typically requires more than one operator, thereby increasing the complexity of the process, and potentially compromising the sterility of the procedure.

A guidewire of a shorter length may be used during the procedure, but during the exchange process, such as when an indwelling therapeutic catheter is exchanged for an aspiration catheter or when an indwelling aspiration catheter is exchanged for a therapeutic catheter, a longer exchange guidewire is substituted for the original guidewire. Also, as is disclosed in U.S. Pat. No. 4,917,103 to Gambale et al., incorporated herein by reference in its entirety, the length of the original guidewire may be extended using a guidewire extension apparatus.

Aspiration catheters may also be of the single operator or "rapid-exchange" (RX) type. An RX aspiration catheter typically includes a tubular catheter shaft with an aspiration lumen extending the entire length thereof and a guidewire shaft having a guidewire lumen of minimal length positioned along a distal portion of the catheter, although some of these catheters are not advanced over guidewires at all. As such, the guidewire is located outside of the aspiration catheter except for a short segment which extends within the guidewire lumen. Therefore, a clinician is able to control both ends of the guidewire while the aspiration catheter is loaded onto the guidewire. The aspiration catheter is then advanced through the patient with only a distal portion of the catheter riding on the guidewire.

While convenient for rapid and simple exchange, RX type catheters typically lack the desired stiffness and pushability for readily advancing the catheter through the tortuous vascular system. Furthermore, use of these catheters increases the likelihood of guidewire entanglement and may lead to damage of the vascular walls due to the tension load applied to the guidewire. Although a single clinician may be able to deploy such an aspiration catheter, the long proximal end of the catheter is still relatively difficult to manipulate, thereby increasing the complexity and duration of the deployment of the aspiration catheter.

Another catheter designed for fast and simple catheter exchange is sold by Medtronic Vascular, Inc. of Santa Rosa, Calif. under the trademarks MULTI-EXCHANGE™, ZIPPER MX™, ZIPPER and/or MX™ (hereinafter referred to as the "MX™ catheter"). An MX catheter is disclosed in U.S. Pat. No. 4,988,356 to Crittenden et al., and in co-pending U.S. patent application Ser. No. 10/116,234, filed Apr. 4, 2002, both of which are incorporated herein by reference in their entireties.

The MX™ catheter includes a catheter shaft having a guideway that extends longitudinally along the catheter shaft and that extends radially from a guidewire lumen to an outer surface of the catheter shaft. A guide member through which the shaft is slidably coupled cooperates with the guideway such that a guidewire may extend transversely into or out of the guidewire lumen at any location along the guideway's length. By moving the shaft with respect to the guide member, the effective over-the-wire length of the MX™ catheter is adjustable.

Additionally, U.S. patent application Ser. No. 10/712,374, filed Nov. 14, 2003, incorporated herein by reference in its entirety, discloses a catheter with a full-length guidewire shaft with a proximal portion comprised of a plurality of independent segments, or clips that hold a guidewire in place along a proximal portion of the catheter and allow access to the guidewire along the proximal portion of the catheter from between adjacent clips.

It is among the general objects of the present invention to provide an alternative catheter design which also allows for fast and simple catheter exchange. What is needed is a catheter which allows for single operator catheter exchange without the use of a guidewire extension. Accordingly, the present invention provides a catheter that includes a single lumen that is configured to receive a guidewire and to perform the function of the catheter.

BRIEF SUMMARY OF THE INVENTION

In one embodiment, the present invention provides a catheter, with a catheter shaft having a catheter lumen, a proximal portion and a distal portion, wherein the distal portion has at least two axially aligned openings traversing from an outer surface to an inner surface of the catheter shaft. The catheter shaft has an expanded portion between the two openings that is offset radially to create a guidewire lumen that is configured to receive a guidewire, wherein the guidewire lumen and the catheter lumen are not separate from each other. In another embodiment, the catheter lumen has a substantially circular cross-section throughout the length of the catheter, while the portion of the catheter comprising the expanded guidewire lumen and the catheter lumen forms a substantially teardrop-shaped lumen. The openings in the guidewire shaft are guidewire-sized openings. A catheter in accordance with the present invention can be any catheter known to one of ordinary skill in the art, including aspiration and delivery catheters.

A catheter according to the present invention may include at least four axially aligned openings with an expanded portion between the first and second openings, a second expanded portion between the third and fourth openings, and a guidewire tracking portion on an exterior surface of the catheter shaft between the second and third openings.

A catheter according to the present invention may be used without blocking or covering the openings in the catheter shaft. In other embodiments of the present invention, when a guidewire is placed within the guidewire lumen such that the guidewire extends through and substantially blocks the openings in the catheter shaft, the amount of fluid that enters or leaves the catheter lumen through the openings during aspiration or delivery is reduced. The openings may further comprise a gasket created by coating the openings with a polymeric material. Such a gasket aids in sealing the openings around the guidewire. In other embodiments, a catheter according to the present invention may further comprise an occlusive device. As the catheter lumen and the guidewire lumen are not separate, this allows for a very low profile catheter, while still maintaining a large lumen for aspiration or delivery.

The present invention also provides for a catheter including a first through $n^{th}$ axially aligned openings, an expanded portion between the first and second axially aligned openings, a guidewire tracking portion between the second and third axially aligned openings, and an expanded portion between the third and fourth axially aligned openings. This pattern is then repeated such that there is an expanded portion between the first two axially aligned openings and an expanded portion between the final two axially aligned openings, n−1 and n.

The present invention also provides a catheter having one axially aligned opening and an expanded portion between the distal tip of the catheter and the first axially aligned opening. In other embodiments, the catheters of the present invention can further comprise a second through $n^{th}$ axially aligned openings, a guidewire tracking portion between the first axially aligned opening and a second axially aligned opening, and an expanded portion between the second and third axially aligned openings, wherein the pattern is repeated such that there is an expanded portion that extends from the final axially aligned opening n through the length of the proximal portion.

In other embodiments, the catheters according to the present invention can further include an aspiration port or a delivery port.

The present invention also provides for methods of making catheters comprising: (a) providing a catheter shaft having a circular lumen, (b) creating at least two axially aligned openings in the shaft, traversing from an outer surface to an inner surface of the shaft; (c) lacing one end of a guidewire lumen mandrel into a first opening, through the circular lumen and back out an adjacent second opening; (d) inserting a large lumen mandrel through the lumen, thereby forcing the guidewire lumen mandrel to expand the shaft radially, thereby creating an expanded portion of the shaft between the two openings; (e) removing the guidewire lumen mandrel to create a guidewire lumen; and (f) removing the large lumen mandrel, creating a catheter where the guidewire lumen and the circular lumen are not separate from each other. The shaft may be heated so as to thermoform the expanded portion. The portion of the catheter comprising the expanded guidewire lumen and the aspiration lumen forms a substantially teardrop-shaped lumen. The openings in the catheter shaft are made in the distal portion of the shaft, and are guidewire-shaped openings.

In other embodiments, (c) may further comprise inserting the guidewire lumen mandrel into a third adjacent opening, through the circular lumen, and back out a fourth adjacent opening. This process is repeated until the guidewire lumen mandrel has been laced through all axially aligned openings, such that both ends of the guidewire lumen mandrel are on the outside of the circular lumen at the completion of the process. In other embodiments, the both ends of the guidewire lumen mandrel can be on the inside of the circular lumen at the completion of the process, or one end can be inside and the other outside. The openings on the catheter shaft may be sealed with a polymeric material to create a gasket in the openings.

In another embodiment, the present invention provides for methods of making a catheter comprising: (a) providing a catheter shaft having a circular lumen and a distal tip; (b) creating at an axially aligned opening in the shaft, the opening traversing from an outer surface to an inner surface of the shaft; (c) inserting one end of a guidewire lumen mandrel into the distal tip, through the circular lumen and out the axially aligned opening; (d) inserting a large lumen mandrel through the circular lumen, thereby forcing the guidewire lumen mandrel to expand the shaft radially, and thereby creating an expanded portion of the shaft between the distal tip and the opening; (e) removing the guidewire lumen mandrel to create a guidewire lumen; and (f) removing the large lumen mandrel, wherein the guidewire lumen and the circular lumen are not separated from each other.

In other such embodiments of the present invention, (c) can further comprise the process of inserting the guidewire lumen mandrel into a second adjacent opening, through the circular lumen, and back out of a fourth adjacent opening, and repeating the process until the guidewire lumen mandrel has been laced through all axially aligned openings, such that the distal end of the guidewire lumen mandrel is on the inside of the circular lumen and the proximal end of the guidewire lumen mandrel is on the inside of the circular lumen at the completion of the process. In other embodiments, the proximal end of the guidewire lumen mandrel can be on the outside of the circular lumen at the completion of the process.

BRIEF DESCRIPTION OF THE DRAWINGS/FIGURES

The foregoing and other features and advantages of the invention will be apparent from the more particular description of the invention, as illustrated in the accompanying drawings. The drawings are not to scale.

DETAILED DESCRIPTION OF THE INVENTION

Embodiments of the present invention are now described with reference to the figures, where like reference numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Figure 1:
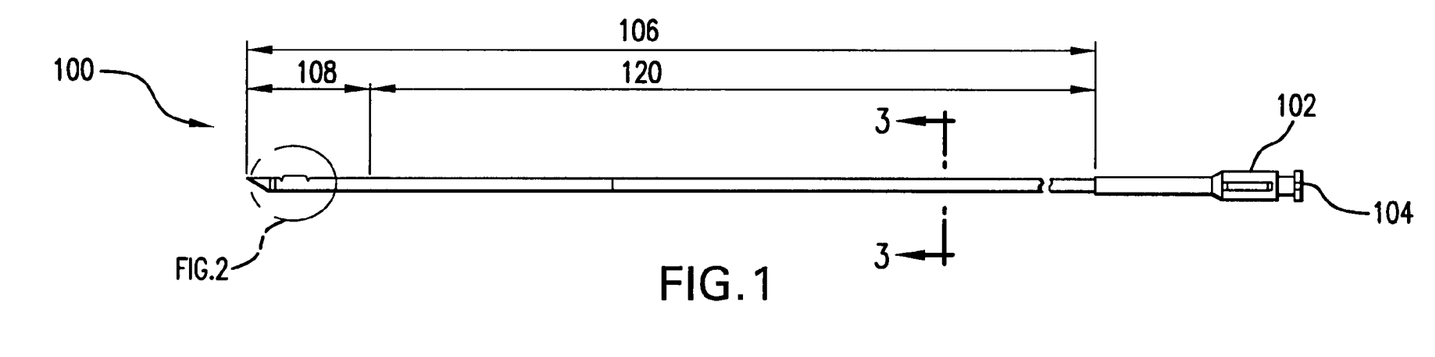
FIG. 1 is a side view of an embodiment of an aspiration catheter in accordance with the present invention.

FIGS. 1-4 illustrate an embodiment of the present invention. In FIG. 1, catheter 100 is illustrated as an aspiration catheter, but the present invention is not so limited and extends to catheters for use in PTCA, vascular drug delivery, aspiration of a treatment site, stent delivery, and/or other diagnostic or therapeutic procedures. In one embodiment, the present invention provides for an aspiration catheter 100 having a catheter shaft 106 with an aspiration lumen 116. Catheter shaft 106 has a distal portion 108 and a proximal portion 120. As used herein, "distal portion" refers to the portion of the catheter farthest from, or in a direction away from, the clinician. In one embodiment, the distal portion extends 30 cm from the most distal end of the catheter. As used herein, "proximal portion" refers to the portion of the catheter nearest or toward the clinician.

Figure 10:
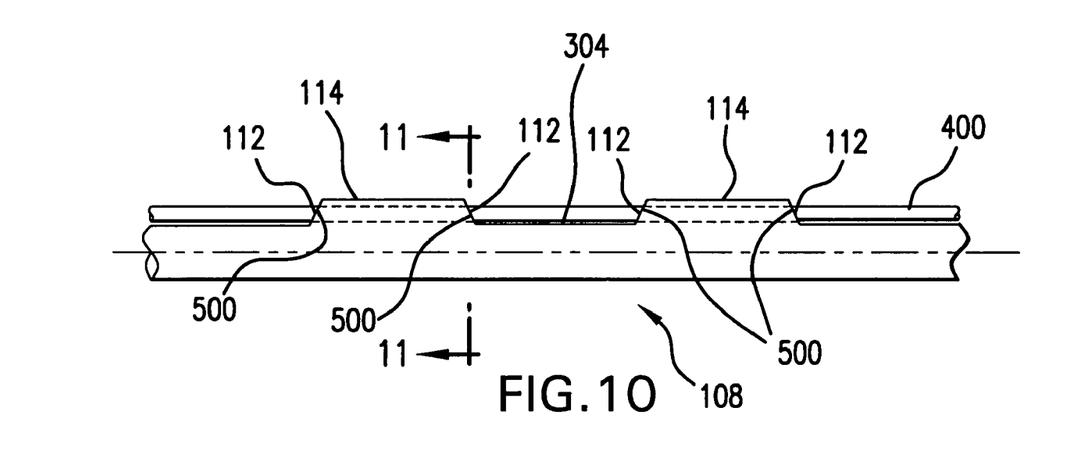
FIG. 10 is a side view of a distal portion of a catheter shaft in accordance with one embodiment of the present invention illustrating the insertion of a guidewire through guidewire-sized openings that comprise gaskets.
Figure 11:
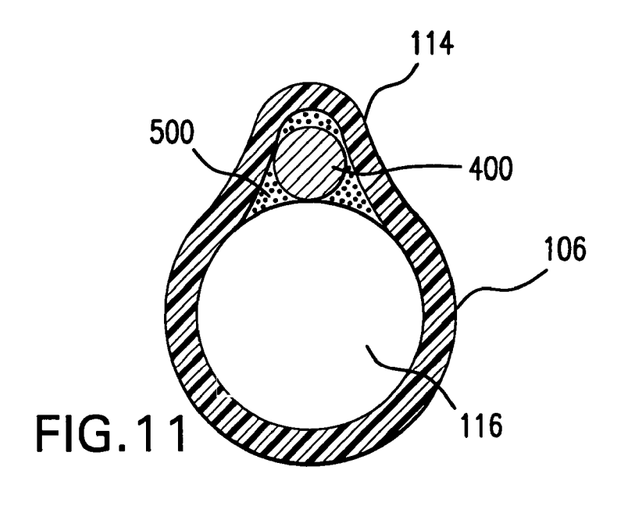
FIG. 11 is a cross-sectional view of the catheter shaft in FIG. 10, taken along line 11-11 in FIG. 10.

According to one embodiment of the present invention, distal portion 108 comprises at least two openings 112 traversing from an outer surface to an inner surface of catheter shaft 106. In certain embodiments of the present invention, openings 112 are axially aligned openings. As used herein, the term "axially aligned openings" means that the openings in the catheter shaft are directly in line with each other along an axis of the catheter shaft. In such embodiments the axially aligned openings 112 are guidewire-sized openings. As used herein, the term "guidewire-sized" means that the diameter of the openings is just slightly larger than, and therefore would fit around and accommodate a guidewire 400, as shown in FIGS. 10 and 11.

Figure 2:
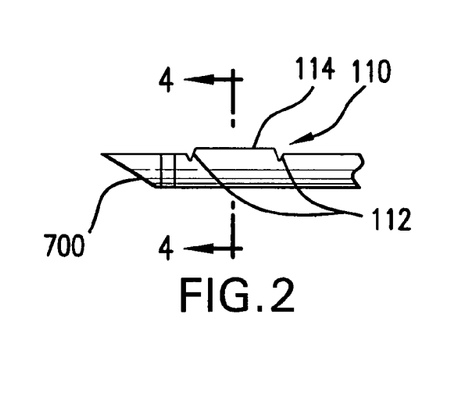
FIG. 2 is an expanded view of the catheter tip in FIG. 1.
Figure 3:
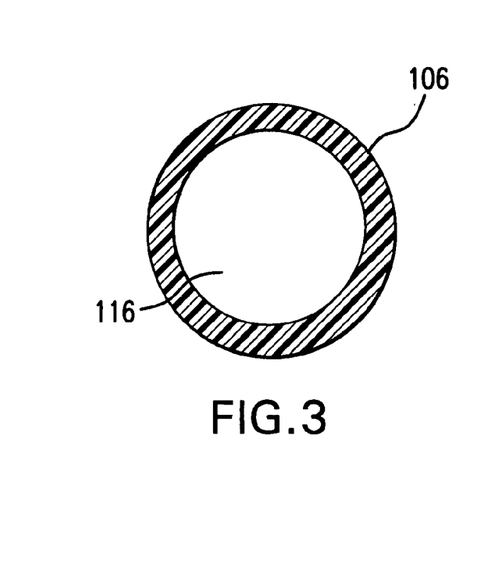
FIG. 3 is a cross-sectional view of the aspiration catheter in FIG. 1, taken along line 3-3 in FIG. 1.
Figure 4:
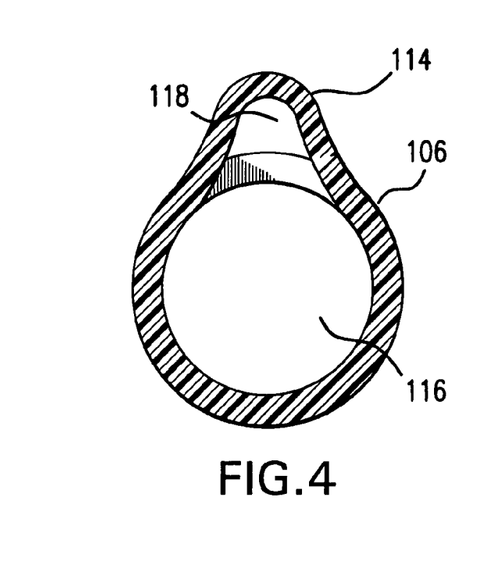
FIG. 4 is a cross-sectional view of the aspiration catheter in FIG. 1, taken along line 4-4 in FIG. 2.

A portion of catheter shaft 106 between openings 112 is expanded radially to create an expanded shaft portion 114, as illustrated in FIG. 2. As such, openings 112 are at an oblique angle to a longitudinal axis of the guidewire lumen 118. By expanding this portion of the catheter shaft outward from the central axis of the catheter shaft, a guidewire lumen 118 is created. The guidewire lumen 118 is created by expanding the aspiration lumen 116, and therefore the two lumens are not separate from each other, as illustrated in FIG. 4. FIG. 4 is a cross-section taken along line 4-4 of FIG. 2 illustrating aspiration lumen 116, and guidewire lumen 118 created by expanding the shaft radially. (Note that the upper section of catheter shaft 106 shown in FIG. 4 does not separate guidewire lumen 118 from aspiration lumen 116, but rather is visible when viewing out of opening 112 toward the direction of the aspiration tip 700 as shown in FIG. 2.) Expanded portion 114 exists between axially aligned openings 112. The remainder of the catheter shaft 106 maintains as a substantially circular cross-sectional aspiration lumen 116 throughout the length of the catheter, as seen in FIG. 3, illustrating a cross-section taken along line 3-3 of FIG. 1.

In one embodiment of the present invention, catheter shaft 106 is a long, continuous tubular catheter shaft with a cross-sectional diameter that is relatively large and having a diameter in a range of 0.7 mm to 18 mm. While the length of catheter shaft 106 may vary depending upon the specific procedure, an appropriate length for aspiration catheter 100 is 145 cm. Catheter shaft 106 may be made of any appropriate polymeric material. Material choice depends on the application and performance requirements. Possible materials used in construction of catheter shaft 106 are PEBAX® (Atochem, France), polyethylene block amide copolymer, polypropylene, polyvinyl chloride, nylon, polyethylene, thermoplastic urethane and blends and laminates thereof.

In embodiments of the present invention, the catheter shaft must have longitudinal compressive strength, i.e., pushability, or stiffness, to permit the catheter to be pushed through the vasculature to distal arterial locations without buckling or undesirable bending of the catheter shaft. It is also desirable, however, for the catheter shaft to be fairly flexible near its distal end, so that the tubular catheter shaft may be navigated through tortuous blood vessel networks. Thus, in one embodiment, the tubular catheter shaft is formed from a polymer such as polyethylene or PEBAX® made to have variable stiffness along its length, with the proximal portion of the tubular catheter shaft being less flexible than the distal portion of the catheter shaft. Advantageously, a tubular catheter shaft of this construction enables a user to more easily traverse the tubular catheter shaft through vasculature that may be difficult to access using conventional catheters of uniform stiffness. This is because the stiffer proximal portion provides the requisite pushability needed to advance the catheter without buckling, while the more flexible distal region is more easily advanced into and through tortuous blood vessel passageways.

Variable stiffness along the length of the catheter shaft may be achieved by forming a polymeric tubular catheter shaft which incorporates a reinforcement along its length. For example, the tubular catheter shaft proximal of any expanded shaft 114 may be provided with a reinforcing braid or coil incorporated into its wall structure. The reinforcement (not shown) can be formed of metal or of various polymers. To achieve variable stiffness, the distal region of the catheter is provided with a braid or coil having a higher braid or coil density than that present in the braid or coil of the proximal region. The lower braid density in the proximal region makes it less flexible, or "stiffer", than the distal region of the catheter.

FIG. 4 illustrates the substantially tear-drop shaped lumen, comprising the guidewire lumen 118 and the aspiration lumen 116, that is formed upon expansion of the shaft to create the guidewire lumen 118. FIGS. 4, 6, 9 and 11 cross-sections illustrate that in accordance with the present invention, the guidewire lumen 118 and the aspiration lumen 116 are not separate from each other and therefore share the same fluid space.

While the aspiration catheter may be utilized without a guidewire, the catheter of the present invention is used in conjunction with a guidewire. In such applications, guidewire 400 is fed into the first, most distal opening, passed through the guidewire lumen 118 formed by the first expanded shaft portion, and out of the next axially aligned opening which forms the other end of the guidewire lumen 118. When passing through the guidewire lumen, the guidewire is in contact with any fluid present in the aspiration lumen, as the guidewire lumen 118 and the aspiration lumen 116 are not separate, as described above.

Figure 5:
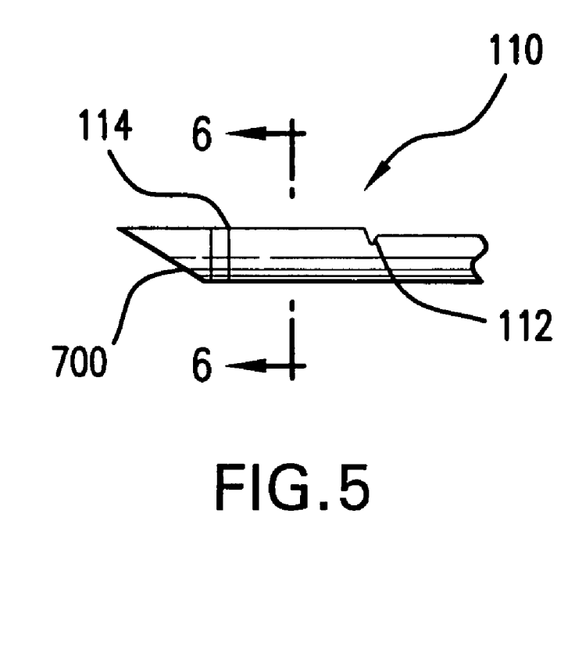
FIG. 5 is an expanded view of a catheter tip showing another embodiment of the present invention.
Figure 6:
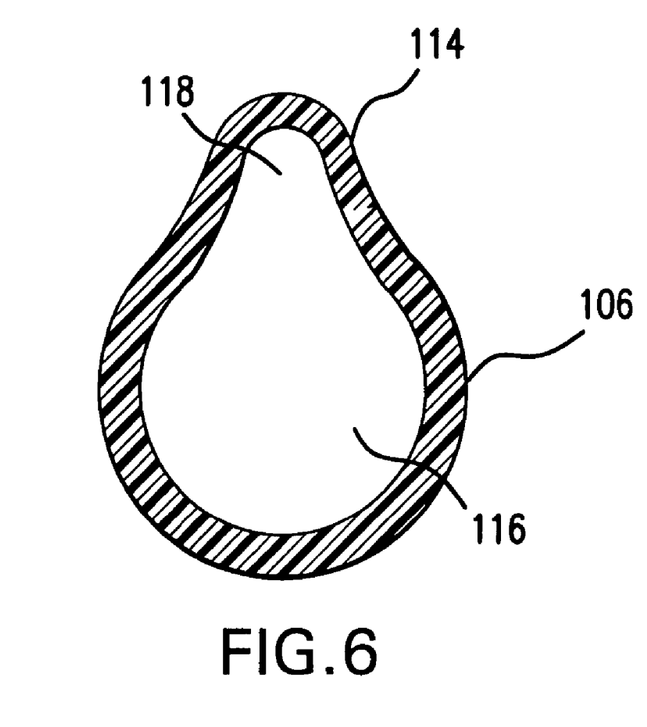
FIG. 6 is a cross-sectional view of the aspiration catheter tip in FIG. 5 taken along line 6-6 in FIG. 5.

In another embodiment of the present invention, distal tip 110 can comprise a single opening 112 that is proximal to aspiration tip 700 as shown in FIG. 5. Expansion of the portion of aspiration shaft 106 between opening 112 and aspiration tip 700 forms expanded portion 114. FIG. 6 shows a cross-sectional view of distal tip 110 taken along line 6-6 of FIG. 5 and shows aspiration lumen 116 and guidewire lumen 118. In certain such embodiments, a guidewire can enter aspiration lumen 116 at aspiration tip 700 and then exit at opening 112. In the distance between aspiration tip 700 and opening 112, the guidewire would be in contact with any fluid that was within aspiration lumen 116. The guidewire can then run outside along the length of the catheter shaft to the operating clinician.

In various embodiments, aspiration catheter 100 further includes an adaptor 102, preferably a female luer fitting at its proximal end. Aspiration catheter 100 may further include an aspiration port 104 to which a vacuum source is attached. Examples of vacuum sources include any container containing a fixed vacuum, such as a syringe, attached to the proximal end of the aspiration catheter at the aspiration port 104. A mechanical pump or bulb or any other appropriate source of a vacuum can also be used.

In other embodiments of the present invention, a guidewire can enter guidewire lumen 118 at aspiration tip 700, exit at opening 112, traverse along the top of the catheter shaft along guidewire tracking portion 304 and then re-enter guidewire lumen 118 at a second opening 112, proximal to the first opening 112 similar to the embodiment shown in FIG. 10. The guidewire can then traverse through the length of the catheter shaft, emerging at aspiration port 104 to allow control and placement by a clinician. In another embodiment of the present invention (not shown), the guidewire can exit guidewire lumen 118 through a third opening 112, further proximal to the second opening 112 and proceed to travel along the top of the catheter shaft. The present invention provides for any number of openings 112 along the length of aspiration shaft 106 through which a guidewire may be laced as it passes from aspiration tip 700 along the length of the catheter shaft.

In another embodiment of the present invention, a distal tip 110 of aspiration catheter 100 is formed from 25D to 40D PEBAX® with a radiopaque filler such as Barium Sulfate ($BaSO_4$). Alternatively, a distal end of the catheter can also be provided with a soft distal tip which is not pre-formed with the tubular catheter shaft, but is instead attached to the catheter shaft in a secondary manufacturing step. The distal tip is preferably soft enough and flexible enough so as to minimize trauma to body vessels as the catheter is advanced and to facilitate navigation of the catheter in tortuous vessels, but must also be stiff enough to avoid collapse during aspiration. In an embodiment, the distal tip is formed as a 0.5 cm sleeve of 25-35D PEBAX® and is bonded to the catheter shaft by use of an adhesive. Alternately, the distal tip may be attached to the catheter shaft by heat bonding, as is known to those of skill in the art.

The distal tip of the aspiration catheter can also be provided with a radiopaque material. Advantageously, radiopaque material serves as a marker to help the user position the catheter inside the patient's body using fluoroscopy. Various well-known radiopaque materials may be used in the distal end to form the marker, such as a platinum or gold band fixedly attached to the distal tip. Alternatively, $BaSO_4$ can be incorporated into the polymer resin itself prior to formation of the tip. The tip may be angled and oblique to provide effective retrieval of particles. The tip angle can be from about 5° to about 90°, usually about 25°. The distal tip of the aspiration catheter can also be blunt, or can be tapered. Side ports can be formed along the distal tip of the catheter to ensure that at least some ports remain open when others are blocked by aspirated material or by the wall of the vessel.

Figure 7:
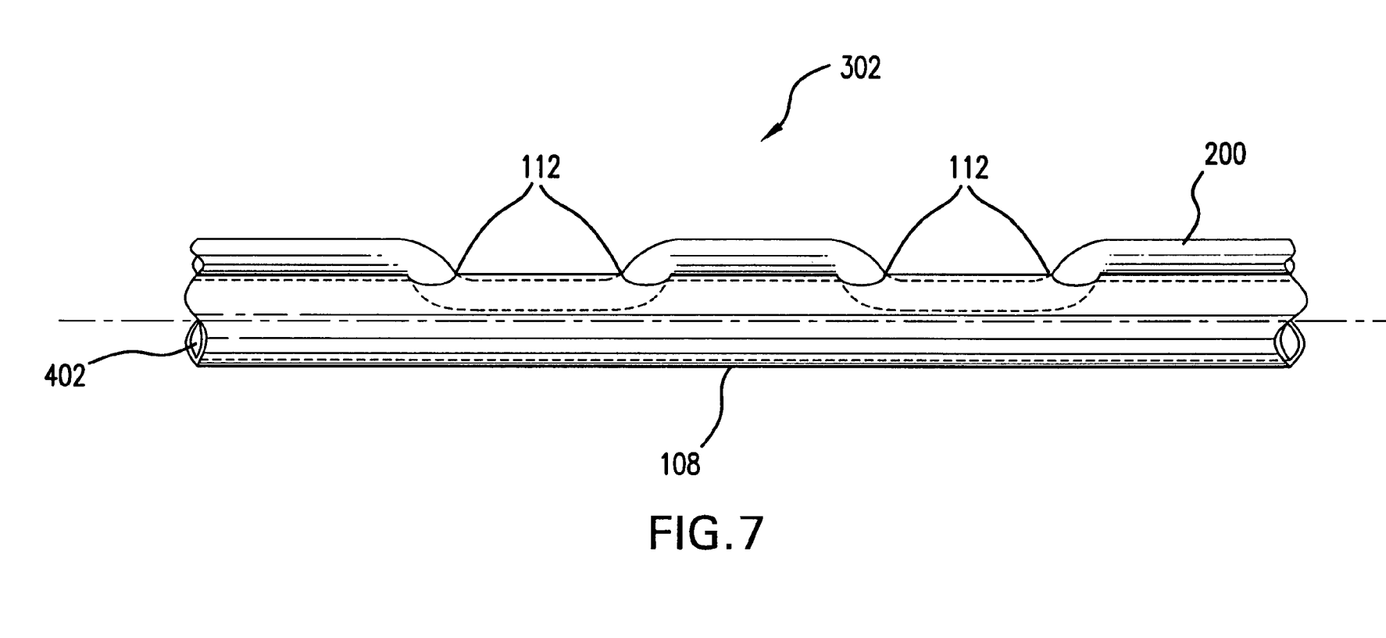
FIG. 7 is a side view of a distal portion of a catheter shaft illustrating the insertion of a guidewire lumen mandrel.
Figure 8:
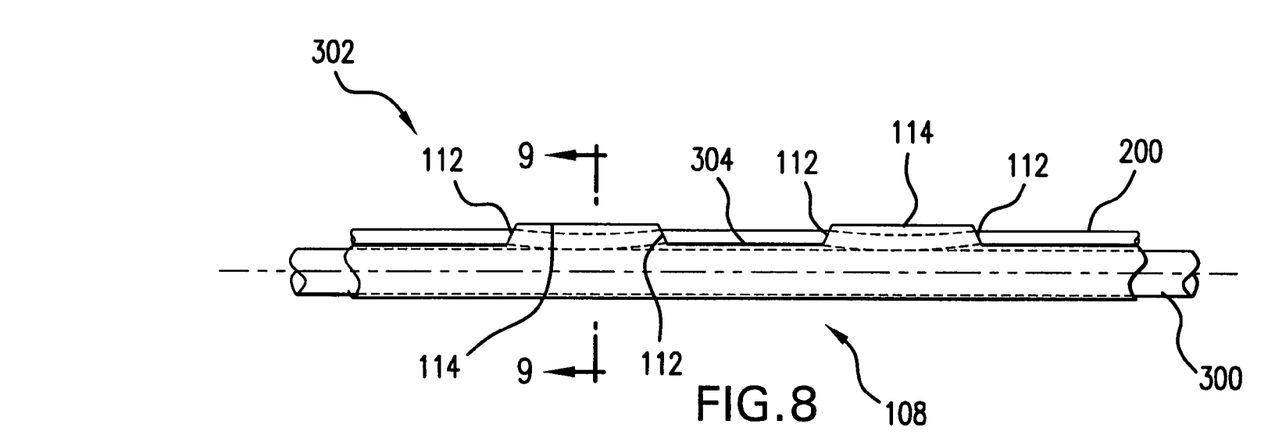
FIG. 8 is a side view of a distal portion of a catheter shaft illustrating the insertion of a guidewire lumen mandrel and a large lumen mandrel, and the formation of expanded shaft portions.

In an embodiment of the present invention shown being formed in FIGS. 7 and 8, an aspiration catheter 302 of the present invention comprises at least four axially aligned openings 112, an expanded portion 114 between the first and second openings 112, a second expanded portion 114 between the third and fourth openings 112, and a guidewire tracking portion 304 on an exterior surface of the catheter shaft between the second and third openings 112. Guidewire tracking portion 304 provides the operator with the ability to monitor and maneuver the guidewire between neighboring expanded portions 114. As illustrated in FIG. 10, guidewire tracking portion 304 is present between two neighboring openings 112. In such a configuration, during loading of a guidewire, the guidewire 400 extends through a first opening 112 at one end of an expanded portion 114, extends through the guidewire lumen 118 where the guidewire would be in contact with any fluid present in the aspiration lumen, extends out of a second opening 112 on other end of the expanded portion 114, extends across the outer surface of the catheter shaft 106 along the guidewire tracking portion 304, enters through a third opening 112 at one end of a second expanded portion 114, extends through a second guidewire lumen 118, and then out of a fourth opening 112 and continues along the outside surface of the catheter shaft 106.

An aspiration catheter according to the present invention can be utilized without a guidewire 400 present in the guidewire lumen 118 as shown in FIG. 4. In such a configuration, the aspiration catheter will function as required, removing debris from the treatment site via an applied partial vacuum. The openings 112 in the catheter shaft 106 do not negatively impact the ability of the catheter to aspirate debris away from the site. The amount of fluid flow through the openings 112 into the aspiration lumen 116 is such that a vacuum is still present at the distal tip 110 to facilitate debris removal.

In other embodiments, when a guidewire 400 is positioned within the guidewire lumen 118, openings 112 are substantially blocked such that the fluid predominantly enters through aspiration tip 700.

In order to reduce the amount of fluid entering the aspiration lumen through the openings even further, a gasket 500 may be created in one or more of the openings 112 to provide a seal around the guidewire 400. FIG. 11 shows an embodiment of the present invention in which gaskets 500 have been created in openings 112 so as to provide a seal around guidewire 400. FIG. 11 shows a cross-section taken along line 11-11 of FIG. 10 illustrating the positioning of guidewire 400 and gasket 500 within opening 112. Gasket 500 is created by coating the openings with a polymeric material. Useful coatings include, but are not limited to, hydrophilic, hydrophobic and antithrombogenic coatings, including heparin, silicone, polyurethane and poly(vinylpyridine) (PVP).

The present invention allows for the guidewire 400, when fed through the guidewire lumen 118, to be held closely to the side of the aspiration lumen 116. As the aspiration lumen and the guidewire lumen are not separate, this allows for a very low profile catheter, while still maintaining a large aspiration lumen. While the guidewire lumen and the aspiration delivery lumen share the same fluid space, the presence of expanded portions 114 of the shaft allow the guidewire 400 to extend outside of the circumference of the aspiration lumen 116, thereby creating a large, substantially circular, aspiration lumen 116 (see FIGS. 4, 9 and 11).

In additional embodiments of the present invention, the aspiration catheter may further comprise an occlusive device. Suggested occlusive devices for use in the present invention include, but are not limited to, balloons, filters, and other mechanical occlusive devices.

In another embodiment, the present invention provides for an aspiration catheter including a first through an $n^{th}$ axially aligned openings. As used herein, "n" refers to an integer, i.e., 1, 2, 3, 4, 5, 6, 7, 8, 9, 10 . . . etc. The present invention therefore encompasses an aspiration catheter that comprises any number of axially aligned openings. The two distalmost axially aligned openings will form the ends of an expanded portion 114 of the catheter shaft that forms guidewire lumen 118. Moving proximally, the next two axially aligned openings will have between them a guidewire tracking portion 304 (See FIG. 8) running along the outer surface of the catheter. Continuing in a proximal direction, the next two axially aligned openings will form the ends of a second expanded portion 114 and comprise a guidewire lumen 118. While this pattern may continue throughout the length of the catheter, however, in one embodiment, it is confined to the distal portion of the catheter shaft 108, extending up to 30 cm from the distal end. In certain such embodiments, the final two openings n−1 and n, n being the most proximal, will be the two ends of an expanded portion 114 of the catheter shaft.

In other embodiments, when a guidewire 400 is fed through the guidewire lumen, it begins on the outside of the catheter shaft, enters the guidewire lumen 118 formed by a first expanded shaft portion 114, exits the guidewire lumen 118, traverses along the outside of the shaft through a guidewire tracking portion 304, enters the guidewire lumen 118 formed by a second expanded shaft portion 114, and then exits the guidewire lumen 118. This pattern is repeated as many times as there are expanded portions 114, so long as the final opening 112 through which the guidewire 400 passes is the most proximal opening of an expanded portion 114. In this embodiment, both the distal and proximal ends of guidewire 400 are on the outside of the catheter shaft at both the most distal and most proximal ends, respectively, of the catheter.

In other embodiments within the scope of the present invention, the final opening, n, may be the distalmost opening of an expanded portion 114 of the catheter shaft that extends from axially aligned opening n, all the way to the proximal end of the catheter, exiting the catheter at the attachment site of adapter 102.

In other embodiments of the present invention, as noted above, the guidewire may enter through aspiration tip 700 and then exit out of the catheter through a first (and in certain embodiments, only) opening 112. The guidewire can then extend all the way to the proximal end of the catheter on the outside of the catheter, or may enter through a second opening 112 and extend all the way to the proximal end of the catheter inside of guidewire lumen 118 that runs the remaining length of the catheter shaft. In other embodiments of the present invention, the catheter shaft can comprise any number of openings 112 throughout its length that allow the guidewire to be laced in and out of various sections of expanded portions 114 comprising guidewire lumen 118 and along various lengths of guidewire tracking portions 304.

As noted above, the present invention extends beyond aspiration catheters, and includes catheters for use in PTCA, vascular drug delivery, aspiration of a treatment site, stent delivery, and/or other diagnostic or therapeutic procedures.

Another embodiment of the present invention provides for delivery catheters with the characteristics and components described throughout the present specification. In certain such embodiments, the present invention provides for a delivery catheter including a catheter shaft having a delivery lumen, a proximal portion and a distal portion, the distal portion having at least two axially aligned openings traversing from an outer surface to an inner surface of the catheter shaft. The shaft includes an expanded portion between the two openings that is offset radially to create a guidewire lumen that is configured to receive a guidewire, wherein the guidewire lumen and the delivery lumen are not separate from each other. In such embodiments, the delivery lumen has a substantially circular cross-section throughout the length of the catheter, while the portion of the catheter having the expanded guidewire lumen and the delivery lumen forms a substantially teardrop-shaped lumen. The openings in the guidewire shaft are guidewire-sized openings that may have gaskets. As discussed throughout, the catheter shaft of a delivery catheter according to the present invention may include any number of openings, and various configurations of guidewire lumens and guidewire tracking portions. In all cases, the guidewire lumens and the delivery lumen are not separate. As noted throughout, when a guidewire is present in the guidewire lumen, it is in contact with any fluid in the delivery lumen.

Delivery catheters of the present invention may further include adaptors and delivery ports as described throughout, and known to the ordinarily skilled artisan. Delivery catheters according to the present invention may be used to deliver any fluid media, including, but not limited to, solutions of enzymes, chemicals and drugs, as may be used to dissolve and treat occlusions.

The present invention also encompasses treatment catheters that include the characteristics and components described throughout. Besides delivering fluid media, treatment catheters may be used to deliver any number of devices, including but not limited to, an atherectomy device, a rheolitic device, a laser and an ultrasound device.

Figure 12:
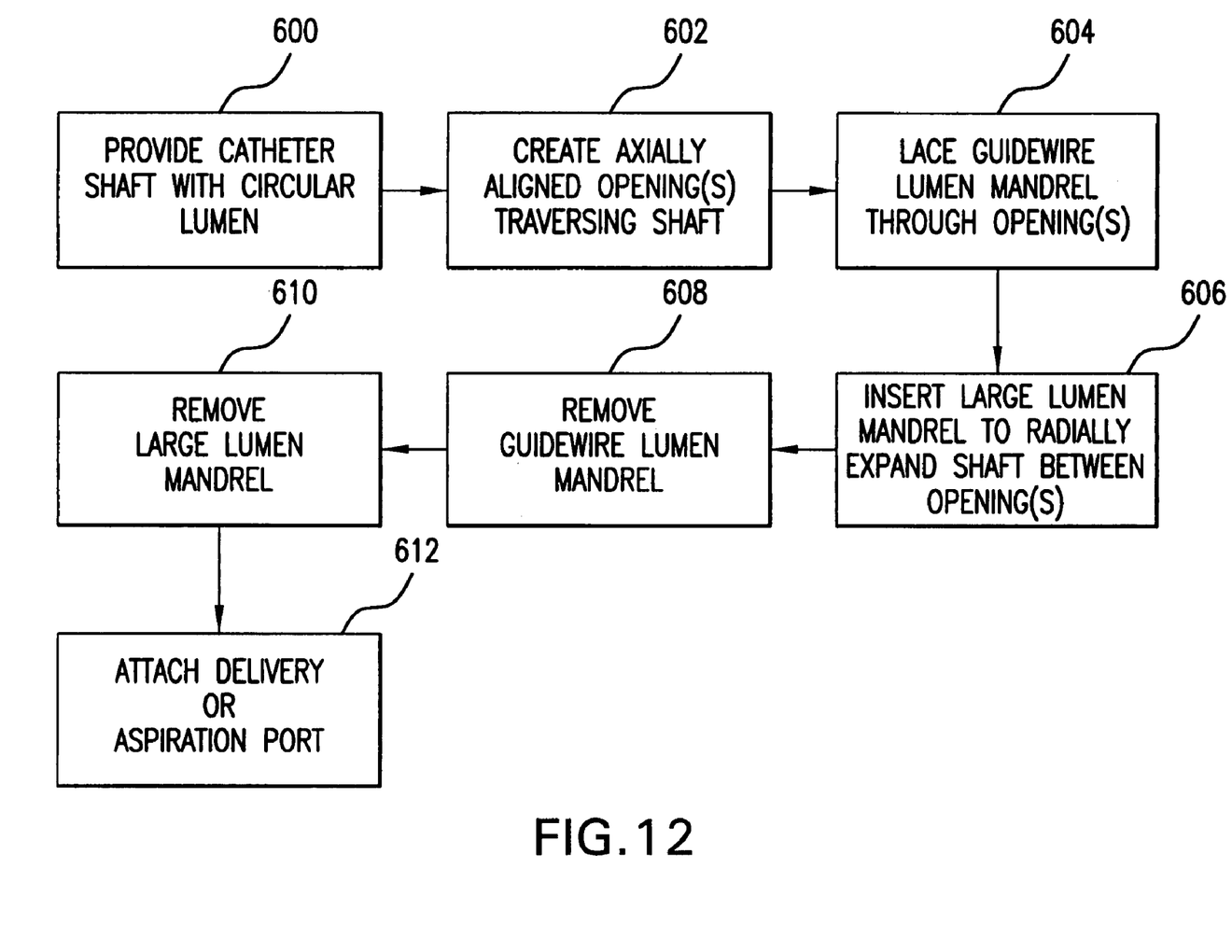
FIG. 12 is a flowchart depicting a method for making a catheter in accordance with one embodiment of the present invention.

As shown in FIG. 12, the present invention also provides methods of making aspiration or delivery catheters comprising: (a) providing a catheter shaft having a circular lumen, step 600 (i.e., cross-section); (b) creating at least two axially aligned openings in the shaft, traversing from an outer surface to an inner surface of the shaft, step 602; (c) lacing one end of a guidewire lumen mandrel into a first opening, through the circular lumen and back out an adjacent second opening, step 604; (d) inserting a large lumen mandrel through the lumen, thereby forcing the guidewire lumen mandrel to expand the shaft radially, thereby creating an expanded portion of the shaft between the two openings, step 606; (e) removing the guidewire lumen mandrel to create a guidewire lumen, step 608; and (f) removing the large lumen mandrel, such that the guidewire lumen and the circular lumen are not separate from each other, step 610. The present invention also provides for methods where the large lumen mandrel is removed prior to the guidewire lumen mandrel. In other embodiments of the present invention, a delivery or aspiration port may then be attached to the catheter, step 612.

FIG. 7 illustrates the distal portion of a catheter shaft 108 with four axially aligned openings 112 traversing from the outer surface to the inner surface of the shaft. Axially aligned openings 112 are guidewire-sized openings that are drilled or punched in the catheter shaft.

A guidewire lumen mandrel 200 illustrated in FIG. 7 is fed through a first opening 112, the guidewire lumen mandrel 200 beginning on the exterior of the catheter shaft, then passing through the first opening 112 into the circular lumen 402 of the catheter, through the circular lumen 402, and back out a second opening 112. The guidewire lumen mandrel 200 is then traversed along the outside of the catheter shaft, fed into a third opening 112, through the circular lumen 402, and back out a fourth opening 112. This lacing process is continued until the guidewire lumen mandrel 200 has been fed through all openings 112. In one embodiment, this process will be performed by beginning with the most distal axially aligned opening 112 and then moving proximally, though it may be performed in the opposite direction. Guidewire lumen mandrel 200 is a continuous, solid piece as illustrated in FIG. 7, though this process may also be performed using separate, individual guidewire lumen mandrels that allow for the formation of the expanded shaft portions 114. Both the guidewire lumen mandrel 200 and the large lumen mandrel 300 can be made of stainless steel.

In other embodiments of the present invention, the distal portion of the catheter shaft may comprise an odd number of openings 112. In certain such embodiments, insertion of the guidewire lumen mandrel 200 begins from the interior of the catheter shaft, then the guidewire lumen mandrel is passed out a first opening 112, traversed along the outside of the catheter shaft, fed into a second opening 112, through the circular lumen 402 of the catheter, and back out a third opening 112. The guidewire lumen mandrel 200 is then traversed along the outside of the catheter shaft, fed into the fourth opening 112, through the circular lumen 402, and back out a fifth opening 112. This lacing process is continued until the guidewire lumen mandrel has been fed through all openings 112 and will result in the guidewire lumen mandrel 200 exiting the circular lumen. This process will be performed by beginning with the most distal opening and then moving proximally, though it can be performed in the opposite direction. In certain such embodiments where the catheter shaft comprises an odd number of openings 112, if insertion the guidewire lumen mandrel 200 beings from the exterior of the catheter shaft, the guidewire lumen mandrel 200 will not exit the circular lumen 402 as in FIG. 7, but will continue to pass through the circular lumen 402, until the guidewire lumen mandrel 200 comes out the proximal end (i.e. closest to the operator) of the catheter. In other embodiments of the present invention, the distal portion of the catheter shaft may comprise any number of openings 112.

In other embodiments of the present invention, the distal portion of the catheter shaft may comprise any number of openings 112 and guidewire lumen mandrel can be inserted into aspiration tip 700, through circular lumen 402, then back out a first opening 112. The guidewire lumen mandrel 200 is then traversed along the outside of the catheter shaft, fed into a second opening 112, through the circular lumen 402, and back out a third opening 112. This lacing process is continued until the guidewire lumen mandrel has been fed through all openings 112. This process will be performed by beginning at aspiration tip 700 and then moving proximally, though it may be performed in the opposite direction. In certain such embodiments where the catheter shaft comprises an odd number of openings 112, the guidewire lumen mandrel will exit the circular lumen 402. In other embodiments where the catheter shaft comprises an even number of openings 112, the guidewire lumen mandrel will not exit the circular lumen 402, but will continue to pass through the circular lumen 402, until the guidewire lumen mandrel 200 comes out the proximal end (i.e. closest to the operator) of the catheter.

FIG. 8 illustrates the distal portion of a catheter shaft with inserted guidewire lumen mandrel 200 and large lumen mandrel 300. Large lumen mandrel 300 is inserted into the distal portion of the catheter shaft with inserted guidewire lumen mandrel 200. Insertion of large-lumen mandrel 300 (either from the distal or proximal end of the catheter shaft) into the catheter shaft with inserted guidewire lumen mandrel forces the guidewire lumen mandrel 200 to expand the distal portion 108 of the catheter shaft as the portions of the guidewire lumen mandrel that were inside the circular lumen 402 are forcibly pushed outward to accommodate the large lumen mandrel 300 in the circular lumen 402. This creates the radially expanded shaft portions 114.

In order to thermoform the expanded shaft portions 114, the distal portion of the catheter shaft with inserted guidewire lumen mandrel and large lumen mandrel 300 may be heat-set. Such a heat-setting process involves elevating the temperature of the catheter shaft above the glass transition temperature of the thermoplastic material, but below the melting temperature thereof.

Following the formation of the expanded shaft portions 114, the guidewire lumen mandrel 200 is removed to create the guidewire lumen 118, and the large lumen mandrel 300 is removed, leaving the substantially circular lumen 116 of the catheter. Removal of the guidewire lumen mandrel 200 and the large lumen mandrel 300 can be done in any order.

Figure 9:
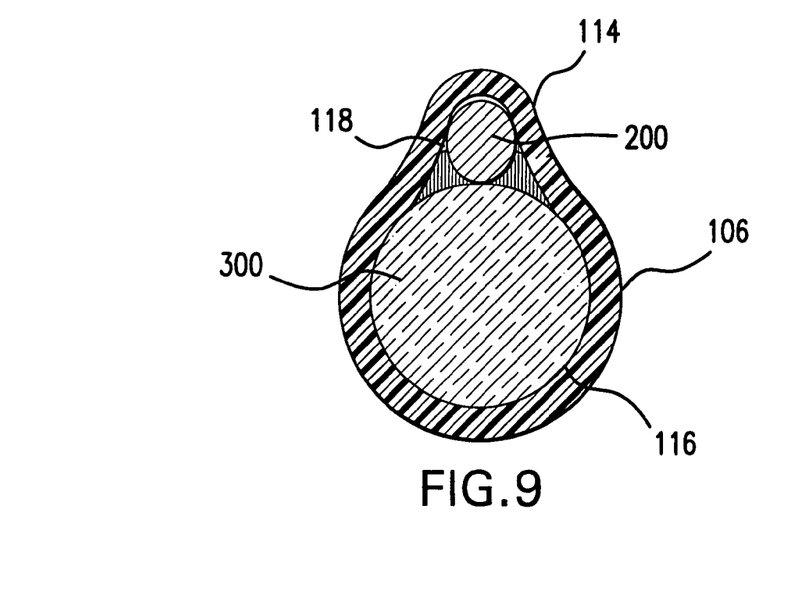
FIG. 9 is a cross-sectional view of the catheter shaft in FIG. 8, taken along line 9-9 in FIG. 8.

FIG. 9 illustrates a cross-section of the catheter shaft in FIG. 8 taken along line 9-9. In sections of the catheter shaft where the expanded portions of the catheter shaft 114 have been created, the guidewire lumen 118 and the circular lumen 116 form a substantially tear-drop shaped lumen, as seen in FIG. 9. The guidewire lumen 118 and circular lumen 116 are not separate, but rather share the same fluid space. FIG. 9 illustrates the position of guidewire lumen mandrel 200 in the guidewire lumen 118 and large lumen mandrel in circular lumen 116. While the catheters of the present invention are functional for their intended purposes without the presence of a guidewire 400 positioned within the guidewire lumen 118, by feeding a guidewire through the guidewire lumen, openings 112 are substantially blocked such that aspiration occurs predominately through aspiration port 700.

Catheters made according to the present invention may be coated on the inner and outer surface with a variety of materials known to those skilled in the art, including but not limited to, hydrophilic, hydrophobic and antithrombogenic coatings, including heparin, silicone, polyurethane and PVP. These coatings can be applied using methods well known in the art. In some embodiments of the present invention, axially aligned openings 112 are coated so as to create gaskets in the openings. In one embodiment, openings 112 are coated with a polymeric material to create gaskets 500. These gaskets provide a sliding seal around guidewire 400.

Catheters made according to the present invention may be any catheters used in PTCA, vascular drug delivery, aspiration of a treatment site, stent delivery, and/or other diagnostic or therapeutic procedures. In one embodiment, the catheters of the present invention are aspiration catheters and delivery catheters.

The aspiration catheters of the present invention may be used to remove plaque and any associated thrombi from a saphenous vein graft as described below. It should be noted that this application is merely exemplary, and that the method of the present invention can be used in other blood vessels and to remove other types of occlusions as well.

Having now fully described the present invention in some detail by way of illustration, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A catheter, comprising:
a catheter shaft having a catheter lumen, a proximal portion and a distal portion, the distal portion of the catheter shaft comprising at least two axially aligned openings traversing from an outer surface to an inner surface of the catheter shaft and a radially offset expanded shaft portion defined between the two openings, wherein a guidewire lumen configured to receive a guidewire extends through the expanded shaft portion such that the guidewire lumen and the catheter lumen are not separate from each other and form a substantially teardrop-shaped lumen within the expanded shaft portion of the catheter shaft.

2. The catheter of claim 1, wherein the catheter is an aspiration catheter.

3. The catheter of claim 1, wherein the catheter is a delivery catheter.

4. The catheter of claim 1, wherein the catheter lumen has a substantially circular cross-section throughout the length of the catheter.

5. The catheter of claim 1, comprising at least four axially aligned openings, a first expanded shaft portion between the first and second openings, and a second expanded shaft portion between the third and fourth openings.

6. The catheter of claim 5, further comprising a guidewire tracking portion on an exterior surface of the catheter shaft between the second and third openings.

7. The catheter of claim 1, further comprising a guidewire within the guidewire lumen such that the guidewire extends through and substantially blocks the openings, thereby reducing the amount of fluid that enters the catheter lumen through the openings.

8. The catheter of claim 7, wherein at least one of the openings further comprises a gasket adapted to form a sliding seal about the guidewire.

9. The catheter of claim 8, wherein the gasket is created by coating the openings with a polymeric material.

10. The catheter of claim 1, wherein the openings are guidewire-sized openings.

11. A catheter, comprising:
a catheter shaft having a catheter lumen, a proximal portion and a distal portion, the distal portion the catheter shaft comprising a plurality of axially aligned openings, a first radially offset expanded shaft portion defined between a first and a second axially aligned opening, a guidewire tracking portion between the second and a third axially aligned opening, and a second radially offset expanded shaft portion defined between the third and a fourth axially aligned opening, wherein the pattern of two radially offset expanded shaft portions separated by a guidewire tracking portion is repeated at least once along the distal portion of the catheter and wherein the catheter lumen is of a substantially teardrop-shape along the expanded shaft portions of the catheter shaft.

12. A catheter, comprising:
a catheter shaft having a catheter lumen, a proximal portion and a distal portion, the distal portion of the catheter shaft comprising a distal tip, a first axially aligned opening traversing from an outer surface to an inner surface of the catheter shaft, and an expanded shaft portion having a tear-drop shaped cross-section defined between the distal tip and the opening such that the expanded shaft portion is offset radially from the remainder of the catheter shaft to create a guidewire lumen therein that is configured to receive a guidewire therethrough, and
wherein the guidewire lumen and the catheter lumen are not separate from each other.

13. The catheter of claim 12, further comprising a plurality of axially aligned openings, wherein a guidewire tracking portion is between the first axially aligned opening and a second axially aligned opening that is proximal of the first axially aligned opening and a second radially offset expanded shaft portion having a tear-drop shaped cross-section is defined between the second axially aligned opening and a third axially aligned opening that is proximal of the second axially aligned opening.

* * * * *